US012648713B2

(12) United States Patent
Attili et al.

(10) Patent No.: US 12,648,713 B2
(45) Date of Patent: Jun. 9, 2026

(54) DEVICE AND METHOD TO DETERMINE THE MEAN/AVERAGE CONTROL OF ASTHMA/COPD OVER TIME AND COMPLIANCE TO TREATMENT

(71) Applicant: Venkata Satya Suresh Attili, Hyderabad (IN)

(72) Inventors: Venkata Satya Suresh Attili, Hyderabad (IN); Anuradha Vutukuri, Hyderabad (IN)

(73) Assignee: Venkata Attili, Hyderabad (IN)

( * ) Notice: Subject to any disclaimer, the term of this patent is extended or adjusted under 35 U.S.C. 154(b) by 1408 days.

(21) Appl. No.: 16/764,761

(22) PCT Filed: May 1, 2018

(86) PCT No.: PCT/IN2018/050267
§ 371 (c)(1),
(2) Date: May 15, 2020

(87) PCT Pub. No.: WO2019/097534
PCT Pub. Date: May 23, 2019

(65) Prior Publication Data
US 2020/0397343 A1     Dec. 24, 2020

(30) Foreign Application Priority Data
Nov. 15, 2017     (IN) ............................. 201741040879

(51) Int. Cl.
*A61B 5/091*          (2006.01)
*A61B 5/00*           (2006.01)
(Continued)

(52) U.S. Cl.
CPC ............ *A61B 5/091* (2013.01); *A61B 5/4833* (2013.01); *A61B 5/7275* (2013.01);
(Continued)

(58) Field of Classification Search
CPC ..... A61B 5/091; A61B 5/4833; A61B 5/7275; A61B 5/082; A61B 5/083–0836;
(Continued)

(56) References Cited

U.S. PATENT DOCUMENTS

| 6,014,890 A | * | 1/2000 | Breen | .................... G01N 25/64 |
| | | | | 73/335.06 |
| 2007/0149891 A1 | * | 6/2007 | George | .................. A61B 5/083 |
| | | | | 600/533 |

(Continued)

FOREIGN PATENT DOCUMENTS

WO     WO-2018044959 A1 *  3/2018   ............... A61B 5/00

*Primary Examiner* — Puya Agahi
(74) *Attorney, Agent, or Firm* — Myers Wolin, LLC

(57)          ABSTRACT

A method to assess the disease status, determine the mean/average control of the disease and monitor the compliance to treatment over a period of time of a respiratory disease, comprising of predicting the degree of airway inflammation and disease activity by measuring the inflammatory markers, evaluating the mucosal integrity/damage by measuring the moisture levels of the exhaled air, evaluating the breathing function and obstruction by measuring the FEV1 value, and evaluating the symptom control by determining the COPD Score.

9 Claims, 1 Drawing Sheet

(51) Int. Cl.
    *G01N 33/497*       (2006.01)
    *G16H 20/40*        (2018.01)
    *G16H 50/30*        (2018.01)

(52) U.S. Cl.
    CPC ........... *G01N 33/497* (2013.01); *G16H 20/40*
             (2018.01); *G16H 50/30* (2018.01); *A61B*
             *2562/0285* (2013.01); *G01N 33/4975*
           (2024.05); *G01N 2800/122* (2013.01); *G01N*
             *2800/52* (2013.01); *G01N 2800/7095*
                            (2013.01)

(58) Field of Classification Search
    CPC ....... A61B 5/087–0871; G01N 33/497; G01N
               2033/4975; G01N 2800/122; G01N
                       2800/52; G16H 50/30
    USPC .................................................. 600/529, 532
    See application file for complete search history.

(56)                 References Cited

U.S. PATENT DOCUMENTS

2007/0266774 A1* 11/2007 Gibson .............. G01N 33/6893
                                            73/53.01
2010/0268106 A1* 10/2010 Johnson ................. B82Y 30/00
                                          600/532
2018/0356429 A1* 12/2018 Morimoto .............. G01N 33/50

\* cited by examiner

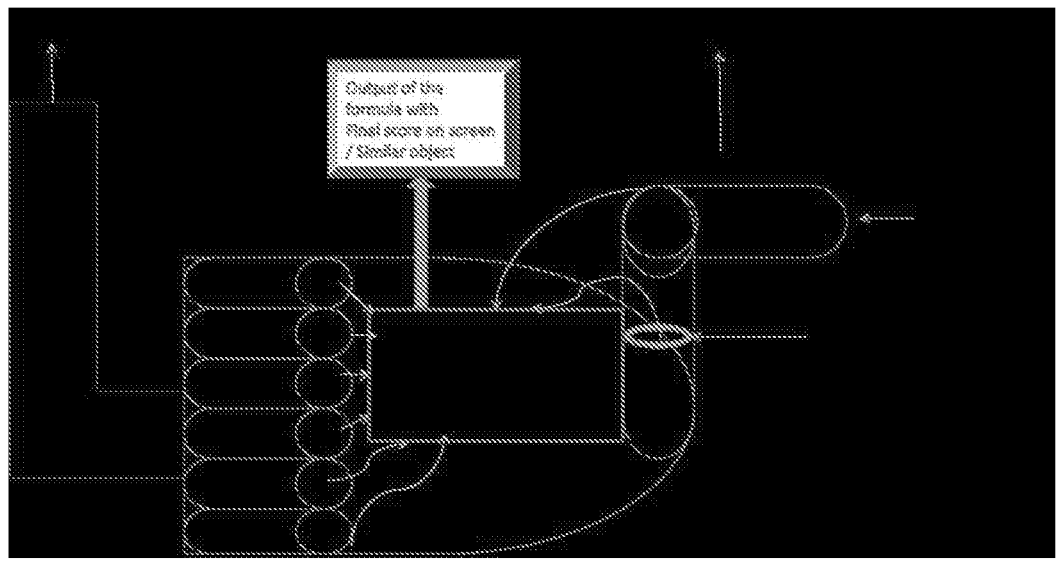

DEVICE AND METHOD TO DETERMINE THE MEAN/AVERAGE CONTROL OF ASTHMA/COPD OVER TIME AND COMPLIANCE TO TREATMENT

TECHNICAL FIELD

This invention relates to a device and method to determine the mean/average control of Asthma/COPD (Chronic Obstructive Pulmonary Disease) over time and compliance to treatment.

BACKGROUND ART

The cumulative number of asthma patients and COPD are more than four hundred million as per the estimate. They are becoming a global social problem with upward surge owing to pollution and smoking habits. One of the published series reported that the true numbers have increased by 20-50% in the past decade in various regions of globe.

Medically COPD is a complex syndrome comprised of airway inflammation, mucociliary dysfunction and consequent airway structural changes, which may present as a syndrome of cough, breathlessness and expectoration of varying severity. The clinical syndromes of Chronic Bronchitis, Emphysema, and Asthma are often overlapping.

Etiopathogeneis of this complex issue is investigated in past and there is a fair bit of knowledge surrounding the same.

To summarize, the inhaled irritants cause inflammatory cells to accumulate.

When activated, these cells initiate an inflammatory cascade that triggers the release of inflammatory mediators such as tumour necrosis factor alpha (TNF-$\alpha$), interferon gamma (IFN-$\gamma$), matrix-metalloproteinases (MMP-6, MMP-9), C-reactive protein (CRP), interleukins (IL-1, IL-6, IL-8) and fibrinogen.

These mediators sustain the inflammatory process and lead to tissue damage as well as a range of systemic effects.

The chronic inflammation is present from the outset of the disease and leads to various structural changes in the lung which further perpetuate airflow limitation, which leads to leads to narrowing of the airways.

The three main factors contribute to this include,
peribronchial fibrosis,
build-up of scar tissue from damage to the airways and
over-multiplication of the epithelial cells lining the airways.

The result is loss of elasticity due destruction of supporting structures and the small airways collapse during exhalation, impeding airflow, trapping air in the lungs and reducing lung capacity [Emphysema].

These irritants also stimulate hypertrophy of the mucous glands in the airway, causing goblet cell metaplasia—leading to healthy cells being replaced by more mucussecreting cell.

Damage to the mucociliary transport system also contributes to this, which presents as excess sputum and cough associated poor ventilation and breathlessness [Chronic bronchitis].

Medical management of this complex syndrome includes drugs like: inhaled steroids and oral steroids; agents that suppress the release of inflammatory mediators; antiallergy agents such as histamine H1 antagonists; P2 agonists that act as bronchodilators; and immunosuppressive agents, along with other symptomatic measures.

The outcomes of this disease are quite variable with few patients having a relatively stable course, while others suffer relentless progression leading to severe breathlessness, frequent acute exacerbations of COPD (AECOPD), respiratory failure and death.

Conventionality the disease and damage of COPD/asthma are measured by static indices like

TABLE 1

| S No | Index | Drawback |
|---|---|---|
| 1 | Radiological markers such as CT emphysema index | by that time we diagnose its too late to act |
| 2 | Molecular changes in lung tissue reflect alterations in lung pathology that occur with disease progression | lung tissue is not routinely accessible, and moreover it is more of prediction for future with limited sensitivity |
| 3 | Cell counts (including neutrophils) and mediators in induced sputum have been associated with lung function and risk of exacerbations | they indicate a snap shot value and act as markers for only one of the patho-physiological process of asthma |
| 4 | Peripheral blood and exhaled air biological markers (biomarkers) include those associated with lung function (reduced CC-16), emphysema severity (increased adiponectin, reduced sRAGE), exacerbations and mortality [increased CRP, fibrinogen, leukocyte count, IL-6, IL-8, and tumor necrosis factor $\alpha$ (TNF-$\alpha$)] including increased YKL-40 with mortality | they are not universally accepted and available |
| 5 | Lung function tests (PFT), particularly the forced expiratory volume in 1 second (FEV1)- The gold standard test | its a snap shot of air way flow "at the time of testing" rather than the average control of asthma" for the obstructive part. However, the restrictive part and reversibility are fairly accurately measured |

TABLE 1-continued

| S No | Index | Drawback |
| --- | --- | --- |
| 6 | Global Initiative for chronic obstructive lung disease (GOLD) guidelines and CAT (COPD assessment testing) | These are routinely practiced and more of subjective phenomena which cannot be quantified and have lot of inter-personal variability |

However, none of them can predict, what is happening or what happened to the airways in past few days. In other words, the average control of asthma over time and compliance to treatment are missed with these testing. Therefore, with the approaches or the methods disclosed in the prior art, the treatment/therapy strategies to control the COPD/asthma are taken considering only the snap shot value of FEV1, with no reasonable sensitivity and specificity, which is resulting in the unpredictability of the control of COPD/asthma over a period of time and failing to delay the progression of the disease. In the methods disclosed in Prior art using Bio markers, the pathological process of COPD at a given time are predicted or the damage happened, so far or the potential for response (mostly non validated). Further, the approaches or the methods disclosed in the prior art cannot predict the disease status in patients who does not exhibit any symptoms of the disease or because of which the existing and ongoing damage to tissue cannot be predicted in the early stages.

SUMMARY OF INVENTION

The invention disclosed herein provides a method to assess the disease status, determine the mean/average control of the disease and monitor the compliance to treatment over a period of time of respiratory diseases, comprising of predicting the degree of airway inflammation and disease activity by measuring the inflammatory markers; evaluating the mucosal integrity/damage by measuring the moisture levels of the exhaled air; evaluating the breathing function and obstruction by measuring the FEV1 value; and evaluating the symptom control by determining the COPD Score. The degree of airway inflammation and disease activity in the method described herein is evaluated by measuring the inflammatory markers comprising of FeNO (fractional exhaled nitric oxide), $H_2O_2$ content of exhaled air, pH of the exhaled air, volatile organic compounds and air exchange & alveolar volume using CO. The respiratory disease is COPD or asthma.

The method as described herein can be used to predict the risk population of respiratory diseases even in cases where there are no signs/symptoms of the disease are observed and therefore would help in prevention of irreversible damage to lungs, thereby improving the quality of life and public health. Further, the method as described herein provides an single instant score which helps the medical practitioner to categorize the patients into (a) well controlled, (b) average/moderately controlled and (c) poorly controlled, which can be used in newly diagnosed patients to assess the degree of inflammation and helps to plan a treatment titration. The single instant score provides the current status of all etiopathogenic agents as well as their status over a given period of time in contrast to the functional assessment only. Furthermore, the method as described herein helps to determine the mean/average control of the disease and monitor the compliance to treatment over a period of time by response prediction to therapy and accordingly change the treatment regime to achieve quick responses to therapy or to quickly control the symptoms, in already diagnosed patient who are undergoing therapy/treatment.

Also, the invention disclosed herein provides a device to assess the disease status, determine the mean/average control of the disease and monitor the compliance to treatment over a period of time of respiratory diseases on a real time basis, comprising of a mouth piece/air inlet, exhaled air outlet, spirometer, multiple sensors, display screen and means for input and output. The device as described herein comprises of moisture measurement sensor, $H_2O_2$ sensor, pH sensor, FeNO sensor, eCO sensor and VOC sensor. The sensors as described herein are electronic/nano/approved and validated sensors. The respiratory disease is COPD or asthma.

The device as described herein further comprises of a software program which provides a single instant score to assess the present status of all etiopathogenic parameters along with the parameters of functional assessment.

The detailed embodiments of the present invention are set forth in accompanying the drawings and described below. Other information, objectives and advantages of this invention would be apparent from the drawing and described in detailed and claimed for their applicability.

BRIEF DESCRIPTION OF DRAWINGS

FIG. 1 shows the detailed schematic representation of the device.

DESCRIPTION OF EMBODIMENTS

The invention disclosed herein provides a method to assess the disease status, determine the mean/average control of the disease and monitor the compliance to treatment over a period of time of respiratory diseases, comprising of predicting the degree of airway inflammation and disease activity by measuring the inflammatory markers; evaluating the mucosal integrity/damage by measuring the moisture levels of the exhaled air; evaluating the breathing function and obstruction by measuring the FEV1 value; and evaluating the symptom control by determining the COPD Score. The degree of airway inflammation and disease activity in the method described herein is evaluated by measuring the inflammatory markers comprising of FeNO (fractional exhaled nitric oxide), $H_2O_2$ content of exhaled air, pH of the exhaled air, volatile organic compounds and air exchange & alveolar volume using CO.

The method as described herein can be used to predict the risk population of respiratory diseases even in cases where there are no signs/symptoms of the disease are observed and therefore would help in prevention of irreversible damage to lungs, thereby improving the quality of life and public health. Further, the method as described herein provides an single instant score which helps the medical practitioner to categorize the patients into (a) well controlled, (b) average/moderately controlled and (c) poorly controlled, which can be used in newly diagnosed patients to assess the degree of inflammation and helps to plan a treatment titration. The single instant score provides the current status of all etiopathogenic agents as well as their status over a given period of time in contrast to the functional assessment only. Furthermore, the method as described herein helps to determine the mean/average control of the disease and monitor the compliance to treatment over a period of time by response prediction to therapy and accordingly change the treatment regime to achieve quick responses to therapy or to quickly control the symptoms, in already diagnosed patient who are undergoing therapy/treatment.

The exhaled breath condensate (EBC), collected from the exhaled breath contains components like condensed water vapor, volatile molecules/compounds (such as nitric oxide, carbon monoxide and hydrocarbons) and non-volatile molecules/compounds (such as urea, GSH, leukotrienes, prostanoids and cytokines). The exhaled breath condensate (EBC) composition reflects the metabolic processes in lungs and is used as a marker for the assessment of airway affection, activity of the inflammatory process and the treatment efficacy. The quantitative composition of EBC gives an indication of the presence of respiratory diseases and also the phase and severity of the disease. A number of inflammatory markers present in the EBC act as biomarkers of disease activity.

Many pulmonary diseases alter the endogenous airway pH homeostasis which induces respiratory symptoms like cough, wheeze, dyspnea and apnea. The air way/EBC pH measurement can be used as a biomarker to assess the endogenous airway acidification in patients with respiratory diseases including stable COPD. In ex-smokers, the airway/EBC pH levels were found to be associated with static hyperinflation, air trapping and diffusing capacity for carbon monoxide. But, no such association is found in the current smokers. The endogenous airway acidification is related to parameters expressing hyperinflation and air trapping in ex-smokers and is indicative of the disease severity. The airway/EBC pH is measured by using electrochemical nano sensor.

The oxygen and nitrogen reactive species or their derivatives in the EBC can be used as indicators of oxidative stress or inflammation and therefore can be used as biomarkers in many lung/respiratory diseases. Carbon monoxide (CO), a low molecular weight gas which is produced endogenously in the human body as a byproduct of heme metabolism, binds to hemoglobin, resulting in decreased oxygen delivery to bodily tissues at toxic concentrations. At physiological concentrations, CO may act as a potential signaling mediator in vascular function and cellular homeostasis. The exhaled CO (eCO), a candidate breath biomarker of pathophysiological states, including smoking status and inflammatory diseases of the lung was chosen. The eCO values is a potential breath biomarker of inflammation in asthma, stable COPD and AECOPD, lung cancer etc. The eCO levels in exhaled breath are measured with the electrochemical (chemiluminescence)/nano technology. The eCO levels are detected by the use of sensors which are sensitive in the range of about 1-500 ppm. According to one embodiment the sensor is a gas sensor adapted from a controlled potential electrolysis method. Alternatively techniques based on infrared laser spectroscopic methods can also be used for the detecting the levels of eCO in the exhaled air.

One of the biomarker in the EBC to measure the oxidative destruction in lung and inflammation of the airways is H2O2. The lung is highly susceptible to oxidative stress in the form of reactive oxygen species/oxygen metabolites like hydrogen peroxide, hydroxyl radical and super oxide ion due to its constant exposure to oxygen. Elevated levels of H2O2 in EBC are indicative of airway inflammation and can be used as an early predictor of the ongoing inflammatory process measured using nano/electrochemical sensor.

Fractional exhaled Nitric Oxide (FeNO) is a measure of airway inflammation and is used as a biomarker for eosnophilic airway inflammation in asthma and other airway diseases. Measurement of fractional nitric oxide (NO) concentration in exhaled breath (FeNO) is a quantitative, non-invasive, simple, and safe method of measuring airway inflammation that provides a complementary tool to other ways of assessing airways disease, including asthma. The magnitude of FeNO increases proportionately to bronchial wall inflammation or induced-sputum eosinophilia as well as to airway hyper-responsiveness. The FeNO is measured by using electrochemical nano sensor.

Exhaled air of a human contains many volatile organic compounds (VOCs) produced during the metabolic processes. The characterization of the exhaled VOCs in patients with respiratory diseases provides the qualitative and quantitative differences in the chemical composition of the exhaled air. The VOCs found in the exhaled air/breath are small organic molecules that are volatile at ambient temperature and include compounds such as hydrocarbons and compounds containing nitrogen, oxygen and sulfur. The exhaled VOCs are characterized by using a sensor or sensor system. According to one embodiment, the senor is an electronic sensor system based on arrays of partially selective gas sensors system. The electronic sensor(s) provide the information about the respiratory profile characterized by a set of various VOCs.

The invention disclosed herein provides a device to assess the disease status, determine the mean/average control of the disease and monitor the compliance to treatment over a period of time of respiratory diseases on a real time basis, comprising of a mouth piece/air inlet, exhaled air outlet, spirometer, multiple sensors, display screen and means for input. The device as described herein comprises of moisture measurement sensor, H2O2 sensor, pH sensor, FeNO sensor, eCO sensor and VOC sensor. The sensors as described herein are electronic nano sensors.

The device as described herein further comprises of a software program which provides a single instant score to assess the present status of all etiopathogenic parameters along with the parameters of functional assessment.

The device as described herein measures the chemical composition of the exhaled air via sensors and inbuilt software program (which is based on exhaled air parameters and flow) gives an instant single score which classifies patients into—

Well controlled,

Average/moderately controlled, and

Poorly controlled categories

The inbuilt software program provides the instant single score by considering the measurements/reading obtained for the following markers/parameters:

FEV1 value—Baseline and previous values to calculate both frequency and amplitude of drifts/fluctuations as entered manually at the beginning of test upon prompting by the device, Patient symptoms and COPD score—manually entered before taking the test [present and previous values], Moisture levels of exhaled air—a marker of mucosal integrity/damage, Markers of inflammation FeNO [Fractional exhaled nitric oxide] absolute value and a reduction from previous score either or considered, $H_2O_2$ content of exhaled air [Range 2-11 micro molar], pH sensor [3-9 range in exhaled air], Volatile Organic Compounds, and Air exchange and alveolar volume using CO.

The inbuilt software program is based on the daily measurement of the FEV1—which indicates the asthma control and using a mathematical algorithm, correlated with the formula as described below:

$$FEV1 \text{ absolute value}^M + \text{change from the previous value}^m + COPD \text{ score}^n + pH^x + CO^y + FeNo^z + H2O2^a + \text{Volatile Organic Compounds}^K$$

FEV I (Tiffeneau-Pinelli index, is a calculated ratio used in the diagnosis of obstructive and restrictive lung disease. It represents the proportion of a person's vital capacity that they are able to expire in the first second of forced expiration to the full vital capacity)—measured as % of exhaled air.

Change of FEV1 means=the present value–previous value of FEV 1.

M is a numeric ranging from 0.06 to 3.98.

COPD score/CAT test (Range of CAT scores from 0-40. Higher scores denote a more severe impact of COPD on a patient's life. The difference between stable and exacerbation patients was five units)—measured as numeric.

N=a value ranging from 0.56-1.38.

pH—Measured as numeric with outer limits capped at 3 to 9.

X=a numeric ranging from 0.8-1.2

CO measured and represented in the range 1-500 ppm, more specifically between 5-36 ppm Y is any value between 0.1 to 2.3

FeNO measured as 6-38 ppb—more specifically 9-20

Z is a value ranging from 0.8-1.6

$H_2O_2$ measured 2.7-22.8 micro moles/Lit

A is a value from 0.7-1.4

VOC (volatile organic compounds) 6 ppbv to 2 ppmv

K is the value ranging from 0.6-1.4

The average control of COPD/asthma over a period of 6 weeks could be predicted with reasonable sensitivity and specificity with above formula.

This shall help physicians to take more informed decisions to adjust therapy thereby delay the progression rather than making decision on snap shot value of FEV1.

The device as disclosed herein measures the following parameters on a real time basis and provides an instant single score to assess the present status of all etiopathogenic agents as well as their status over a given period of time, classification of score to stratify patients, predict disease control in near future and potential complications, and Standardized score for response to therapy, in contrast to the functional assessment only.

Inflammatory markers—to predict the degree of airway inflammation and disease activity.

Moisture levels of exhaled air—a marker of mucosal integrity/damage.

FEV1 [variation from the baseline and average drift—both frequency and amplitude of drifts/fluctuations]—Marker of breathing function and obstruction.

COPD Score—a marker of symptom control.

The instant single score provided by the device described herein reflects the accurate indication of average COPD/asthma status, recent past, existing and ongoing damage to tissue and to prevent irreversible damage to lungs by early intervention, response prediction to medical management of COPD/asthma and optimize treatment which will help the medical professional to avoid both over and under treatment.

The invention claimed is:

1. A method implemented using a computational system to predict a disease status, determine a mean/average control of disease or monitor a compliance to treatment over a period of time of respiratory diseases, the method comprising:

a. obtaining and analyzing measurements of multiple inflammatory markers, including fractional exhaled nitric oxide (FeNO), hydrogen peroxide ($H_2O_2$), pH, volatile organic compounds (VOCs), and carbon monoxide (CO), wherein the analyzing is performed by an inbuilt software program of a device configured to dynamically adjust a contribution weight of each of the multiple inflammatory markers based on real-time inputs and stored historical data;

b. evaluating a mucosal integrity and damage by measuring moisture levels of exhaled air using multiple sensors, wherein the multiple sensors provide input to the inbuilt software program for comprehensive analysis;

c. evaluating breathing function and obstruction by measuring a Forced Expiratory Volume in 1 second (FEV1) value, wherein FEV1 measurements are stored and processed by the inbuilt software program to compute FEV1 trends over time;

d. evaluating a symptom control by determining a Chronic Obstructive Pulmonary Disease (COPD) Score, wherein the COPD Score is calculated using a multi-parameter computational model executed by the inbuilt software program, the multi-parameter model integrating data from the measured multiple inflammatory markers, computed FEV1 trends, evaluated mucosal integrity, and patient-reported symptom inputs scores;

e. classifying the patient into one of a plurality of disease control categories based on the COPD Score, wherein each category is defined by a predefined numerical COPD Score range prestored in a memory of the device; and f. adjusting a treatment regimen for the respiratory disease by administering or modifying inhaled corticosteroid therapy when the classified COPD score range corresponds to a lower level of disease control.

2. The method according to claim 1, wherein the multiple inflammatory markers further comprise non-volatile compounds selected from cytokines, leukotrienes, and prostanoids, detected in Exhaled Breath Condensate (EBC).

3. The method according to claim 1, wherein one of the respiratory diseases is COPD or asthma.

4. A device to assess the disease status, determine the mean/average control of the disease and monitor the compliance to treatment over a period of time of respiratory diseases on a real-time basis, said device being configured to perform the method of claim 2, said device comprising:

a mouthpiece/air inlet configured to collect exhaled air, measure inflammatory markers using integrated electronic nano-sensors;

an exhaled air outlet providing a flow path for sensing with minimal analyte-concentration present within the exhaled breath volume using integrated sensors;

a spirometer configured to evaluate the breathing function and obstruction by measuring the FEV1 value;

multiple sensors configured to evaluate the mucosal integrity and damage by measuring the moisture levels of the exhaled air, wherein the sensors include a moisture measurement sensor, an $H_2O_2$ sensor, a pH sensor, an FeNO sensor, an eCO sensor, and a VOC sensor;

a memory storing predefined numerical COPD score ranges; and an inbuilt software program of the device configured to:

receive measurement data from the sensors and spirometer;

dynamically adjust the contribution of inflammatory markers, FEV1 data, mucosal integrity measurements, and symptom scores using a weighted parameter analysis method;

compute FEV1 trends over time;

calculate a Chronic Obstructive Pulmonary Disease (COPD) score using a multi-parameter computational model integrating inflammatory marker data, FEV1 trends, mucosal integrity measurements, and patient-reported symptom inputs;

classify patients into one of a plurality of disease control categories based on the COPD score, wherein each category corresponds to one of the predefined numerical COPD Score ranges stored in the memory; and generate a control signal configured to initiate or modify inhaled corticosteroid therapy when the classified COPD score range corresponds to a lower level of disease control.

5. The device according to claim 4, wherein the multiple sensors are electronic nano-sensors for measurement of the multiple inflammatory markers.

6. The device according to claim 4, wherein the spirometer is a running spirometer capable of measuring FEV1 and other functional lung markers.

7. The device according to claim 4, wherein the inbuilt software program is configured to calculate a single instant score to assess the present status of all etiopathogenic parameters along with the parameters of functional assessment, including FEV1, mucosal integrity, inflammatory markers, and symptom scores.

8. The method according to claim 1, wherein the COPD score is calculated by utilizing a disease-specific computation model for analyzing respiratory disease status, wherein the disease-specific computation model calculates a composite score based on the following formula:

$$\text{Composite Score}=\text{FEV1}_{absolute\ value}{}^{M}+(\text{Change of FEV1})^{m}+\text{COPD score}^{n}+\text{pH}^{x}+\text{CO}^{y}+\text{FeNO}^{z}+\text{H}_2\text{O}_2{}^{a}+\text{VOC}^{k}$$

where:

$\text{FEV1}_{absolute\ value}$ represents the forced expiratory volume in 1 second, measured as a percentage of exhaled air, Change of FEV1 is defined as the present value minus the previous value of FEV1, M ranges from 0.06 to 3.98, m represents a numeric value indicating change in FEV1, COPD score is determined using a CAT test ranging from 0-40, n ranges from 0.56 to 1.38, pH is measured as numeric with outer limits capped at 3 to 9, x ranges from 0.8 to 1.2, CO is measured in the range of 1-500 ppm, y ranges from 0.1 to 2.3, FeNO is measured as 6-38 ppb, z ranges from 0.8 to 1.6, H2O2 is measured as 2.7-22.8 micro moles/Lit, a ranges from 0.7 to 1.4, VOC (volatile organic compounds) are measured as 6 ppbv to 2 ppmv, and k ranges from 0.6 to 1.4.

9. The device according to claim 4, wherein the COPD score is calculated by utilizing a disease-specific computation model for analyzing respiratory disease status, wherein the disease-specific computation model calculates the composite score based on the following formula:

$$\text{Composite Score}=\text{FEV1 absolute value } M+(\text{Change of FEV1})m+\text{COPD score}n+\text{pH}x+\text{CO}y+\text{FeNO}z+\text{H2O2}a+\text{VOC}k$$

where:

FEV1 absolute value represents the forced expiratory volume in 1 second, measured as a percentage of exhaled air, Change of FEV1 is defined as the present value minus the previous value of FEV1, M ranges from 0.06 to 3.98, m represents a numeric value indicating change in FEV1, COPD score is determined using a CAT test ranging from 0-40, n ranges from 0.56 to 1.38, pH is measured as numeric with outer limits capped at 3 to 9, x ranges from 0.8 to 1.2, CO is measured in the range of 1-500 ppm, y ranges from 0.1 to 2.3, FeNO is measured as 6-38 ppb, z ranges from 0.8 to 1.6, H2O2 is measured as 2.7-22.8 micro moles/Lit, a ranges from 0.7 to 1.4, VOC (volatile organic compounds) are measured as 6 ppbv to 2 ppmv, and k ranges from 0.6 to 1.4.

\* \* \* \* \*